United States Patent
Berg

Patent Number: 5,405,505
Date of Patent: Apr. 11, 1995

[54] SEPARATION OF BENZENE FROM CLOSE BOILING HYDROCARBONS BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 180,966

[22] Filed: Jan. 14, 1994

[51] Int. Cl.$^6$ ............................ B01D 3/36; C07C 7/06
[52] U.S. Cl. ................................. 203/58; 203/60; 203/62; 203/63; 203/66; 585/860; 585/864; 585/865; 585/866
[58] Field of Search .................... 203/63, 60, 62, 58, 203/66; 585/865, 866, 864, 862, 860, 804

[56] References Cited

U.S. PATENT DOCUMENTS

| | | | |
|---|---|---|---|
| 2,279,194 | 4/1942 | Field | 203/60 |
| 2,313,536 | 3/1943 | Greenburg | 203/62 |
| 2,313,538 | 3/1943 | Greenburg | 585/866 |
| 2,352,534 | 6/1944 | Greenburg | 203/58 |
| 2,356,240 | 8/1944 | Hamlin | 203/63 |
| 2,618,591 | 11/1952 | Anderson | 203/66 |
| 2,890,154 | 6/1959 | Maisel | 203/65 |
| 4,514,262 | 4/1985 | Berg | 203/63 |

Primary Examiner—Wilbur Bascomb, Jr.

[57] ABSTRACT

Benzene is difficult to separate from cyclohexane or cyclohexene by conventional distillation or rectification because of the close proximity of their boiling points. Benzene can be readily separated from cyclohexane or cyclohexene by using azeotropic distillation. Effective agents are: for benzene from cyclohexane, dimethoxymethane; for benzene from cyclohexene, methanol.

3 Claims, No Drawings

SEPARATION OF BENZENE FROM CLOSE BOILING HYDROCARBONS BY AZEOTROPIC DISTILLATION

FIELD OF THE INVENTION

This invention relates to a method for separating benzene from close boiling hydrocarbons using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plate to effect the same separation or make possible a greater degree of separation with the same number of plates. The azeotrope forming agent is introduced with the feed to a continuous column. The azeotrope forming agent and the more volatile component are taken of as overhead product and the less volatile components come off as bottoms product. The usual methods of separating the azeotrope former from the more volatile component are cooling and phase separation or solvent extraction.

Benzene boils at 80.1° C. The hydrocarbons boiling closest to benzene are cyclohexane, B.P. 80.8° C. and cyclohexene, B.P. 83.2° C. The relative volatility of benzene to cyclohexane as 1.02, of benzene to cyclohexene is 1.1.

TABLE 1

Theoretical and Actual Plates Required vs. Relative Volatility for Benzene-Cyclohexane-Cyclohexene Separation

| Relative Volatility | Theoretical Plates Required At Total Reflux, 99% Purity | Actual Plates Required, 75% Eff. |
|---|---|---|
| 1.02 | 470 | 630 |
| 1.1 | 96 | 128 |
| 1.2 | 50 | 67 |
| 1.5 | 23 | 31 |
| 2.0 | 14 | 19 |
| 2.4 | 11 | 15 |
| 2.6 | 10 | 14 |

Table 1 shows that benzene cannot be separated practically from cyclohexane by conventional rectification. To separate benzene from cyclohexene in 99% purity requires 128 actual plates. For an agent giving a relative volatility of 2.0, nineteen actual plates are required, with 2.6 it is only fourteen plates.

OBJECTIVE OF THE INVENTION

The object of this invention is to provide a process or method of azeotropic distillation that will enhance the relative volatility of benzene to cyclohexane and cyclohexene in their separation in a rectification column. It is a further object of this invention to identify certain organic compounds that are stable, are effective azeotropic distillation agents and can be recycled to the azeotropic distillation column with little decomposition.

SUMMARY OF THE INVENTION

The objects of this invention are provided by a process for the separation of benzene from cyclohexane and cyclohexene which entails the use of certain organic compounds when employed as the agent in azeotropic distillation.

DETAILED DESCRIPTION OF THE INVENTION

I have discovered that certain organic compounds will effectively increase the relative volatility between benzene and cyclohexane and between benzene and cyclohexene when employed as the agent in azeotropic distillation. Table 2 summarizes the data obtained with these agents.

TABLE 2

Effective Azeotrope Formers For Separating Benzene From Cyclohexane and/or Cyclohexene

| Compounds | Relative Volatility Cyclohexane-Benzene | Relative Volatility Cyclohexene-Benzene |
|---|---|---|
| Acetonitrile | 1.43 | 1.75 |
| Isopropyl ether | 1.3 | 1.55 |
| Amyl methyl ether | 1.85 | 1.25 |
| Methanol | 1.6 | 1.3 |
| Ethanol | 2.2 | — |
| Acetone | — | 2.1 |
| Methyl acetate | 2.4 | 2.35 |
| Isopropanol | 1.5 | 1.2 |
| t-Butanol | 1.3 | — |
| Methyl ethyl ketone | 1.6 | 1.35 |
| Dimethoxymethane | 1.78 | 1.2 |
| 2,2-Dimethoxypropane | 1.65* | — |
| Ethyl acetate | 1.6 | 1.25 |
| 1,3-Dioxolane | 1.75 | 1.3 |
| Tetrahydrofuran | — | 1.25 |

*Brings benzene out as overhead product

The agents which are effective are methanol, ethanol, isopropanol t-butanol, isopropyl ether, amyl methyl ether, methyl acetate, ethyl acetate, methyl ethyl ketone, acetonitrile, acetone, dimethoxymethane, 1,3-dioxolane, 2,2-dimethoxypropane and tetrahydrofuran.

THE USEFULNESS OF THE INVENTION

The usefulness or utility of this invention can be demonstrated by referring to the data presented in Tables 1 and 2. All of the successful agents show that benzene can be separated from cyclohexane and/or cyclohexene by means of azeotropic distillation in a rectification column and that the ease of separation as measured by relative volatility is considerable.

WORKING EXAMPLES

Example 1

Eighty grams of benzene, 20 grams of cyclohexene and 50 grams of methanol were charged to a vapor-liquid equilibrium still and refluxed for twelve hours. Analysis indicated a vapor composition of 89.1% benzene, 10.9% cyclohexene, a liquid composition of 91.7% benzene, 8.3% cyclohexene which is a relative volatility of 1.35.

Example 2

Sixty grams of benzene, 60 grams of cyclohexane and 70 grams of dimethoxymethane were charged to a glass perforated plate rectification column containing 7.3 theoretical plates. After four hours at total reflux, overhead and bottoms samples were taken and analysed by gas chromatography. The overhead was 97.9% cyclohexane, 2.1% benzene; the bottoms was 41.8% cyclohexane, 58.2% benzene which is a relative volatility of 1.78.

I claim:

1. A method for recovering benzene from a mixture of benzene and cyclohexane which comprises distilling a mixture of benzene and cyclohexane in the presence of an azeotrope forming agent, recovering the cyclohexane and the azeotrope forming agent as overhead product and obtaining the benzene from the stillpot, wherein said azeotrope forming agent consists of one material selected from the group consisting of isopropyl ether, amyl methyl ether, ethyl acetate, methyl ethyl ketone, acetonitrile, dimethoxymethane and 1,3-dioxolane.

2. A method for recovering cyclohexane from a mixture of cyclohexane and benzene which comprises distilling a mixture of cyclohexane and benzene in the presence of an azeotrope forming agent, recovering the benzene and the azeotrope forming agent as overhead product and obtaining the cyclohexane from the stillpot, wherein said azeotrope forming agent is 2,2-dimethoxypropane.

3. A method for recovering benzene from a mixture of benzene and cyclohexene which comprises distilling a mixture of benzene and cyclohexene in the presence of an azeotrope forming agent, recovering the cyclohexene and the azeotrope forming agent as overhead product and obtaining the benzene from the stillpot, wherein said azeotrope forming agent consists of one material selected from the group consisting of acetonitrile, isopropyl ether, amyl methyl ether, methanol, isopropanol, acetone, methyl ethyl ketone, methyl acetate, dimethoxymethane, ethyl acetate, 1,3-dioxolane and tetrahydrofuran.

* * * * *